United States Patent [19]

Khanna et al.

[11] Patent Number: 4,950,612
[45] Date of Patent: Aug. 21, 1990

[54] PEROXY ACID PRETREATMENT IN VITAMIN $B_{12}$ ASSAY

[75] Inventors: Pyare L. Khanna, Fremont; Robert T. Dworschack, Antioch, both of Calif.

[73] Assignee: Microgenics Corporation, Concord, Calif.

[21] Appl. No.: 133,501

[22] Filed: Dec. 16, 1987

[51] Int. Cl.$^5$ ............................................. G01N 33/82
[52] U.S. Cl. ........................................ 436/505; 435/7; 436/501; 436/174; 436/175; 436/177; 436/178; 436/811; 436/825; 436/826
[58] Field of Search ............... 436/501, 505, 174, 175, 436/177, 178, 811, 825; 435/7

[56] References Cited

U.S. PATENT DOCUMENTS

| | | | |
|---|---|---|---|
| 3,993,436 | 11/1976 | Fujinuma | 424/71 X |
| 4,451,571 | 5/1984 | Allen | 436/505 |
| 4,456,689 | 6/1984 | Witty et al. | 436/505 X |
| 4,629,785 | 12/1986 | McCaffery, III | 530/415 |
| 4,668,620 | 5/1987 | Armenta et al. | 436/825 X |
| 4,703,001 | 10/1987 | Vodian et al. | 436/825 X |

OTHER PUBLICATIONS

Ithakissios, D. et al., "Room Temperature Radioassay for $B_{12}$ with Oyster Toadfish (Opsanus tau) Serum as Binder", Clinical Chemistry, vol. 26, No. 2, 1980, pp. 323–326.
Faulkner, W. et al., (ed), Selected Methods for the Small Clinical Chemistry Laboratory, American Association for Clinical Chemistry (Washington, DC) 1982, vol. 9, pp. 13–14.
Tietz, N. (ed), Textbook of Clinical Chemistry, W. B. Saunders Company (Philadelphia), 1986, p. 815.

*Primary Examiner*—Esther M. Kepplinger
*Assistant Examiner*—Carol A. Spiegel
*Attorney, Agent, or Firm*—Barbara Rae-Venter

[57] ABSTRACT

Serum samples for vitamin $B_{12}$ analysis can be pretreated using a combination of peroxy acid and dithiothreitol. The pretreatment makes vitamin $B_{12}$ bound to serum binding proteins available for analysis by any of a variety of currently available assay techniques. The pretreatment finds particular use in an assay using solid phase intrinsic factor as a specific binding protein.

11 Claims, No Drawings

PEROXY ACID PRETREATMENT IN VITAMIN $B_{12}$ ASSAY

INTRODUCTION

1. Technical Field

This invention relates to methods for making vitamin $B_{12}$ available in a serum sample, and freeing the vitamin $B_{12}$ from endogenous serum binding proteins for subsequent determination of the serum vitamin $B_{12}$ concentration.

2. Background

The concentration of vitamin $B_{12}$ in serum is the best routine measure of vitamin $B_{12}$ deficiency However, the majority of vitamin $B_{12}$ in blood is bound to proteins. As vitamin $B_{12}$ is absorbed into the circulation, it binds to transcobalamin II, a plasma $\beta$-globulin. Two other transcobalamins (I and III) are also present in plasma which bind vitamin $B_{12}$. In order to accurately measure the amount of vitamin $B_{12}$ present in a serum sample, it is necessary to pretreat the sample to release the vitamin $B_{12}$ from the various serum binding proteins.

Existing vitamin $B_{12}$ binding assays have used a variety of methods for pretreating a serum sample to release vitamin $B_{12}$ from the serum binding proteins. These methods have included heating the sample (the "boil" method) at 100° C. for a sufficient period of time to destroy the endogenous serum binding proteins and the so called "no boil" method in which the sample is treated with sodium hydroxide at pH 12-13. Boil procedures interrupt work flow and are not conducive to automation since it is necessary to first heat the sample and then bring it to room temperature before addition of other reagents. The no boil procedures do not completely denature anti-intrinsic factor antibodies which may be present. There is therefore substantial interest in being able to rapidly and efficiently release vitamin $B_{12}$ from endogenous serum binding proteins as well as to inactivate other factors which may influence the outcome of the assay procedure.

Relevant Literature

A method for releasing vitamin $B_{12}$ from endogenous serum binding proteins using a releasing agent comprising an organic solvent, a reducing agent and cyanide ions is disclosed in U.S. Pat. No. 4,300,907, issued Nov. 17, 1981 to Mansbach and McCarter. A method for denaturing vitamin $B_{12}$ binding protein using a combination of heat and a denaturing agent such as urea is disclosed in U.S. Pat. No. 4,332,786, issued June 1, 1982 to Cabelli and Groman, Gutcho and Mansbach, Clin. Chem. (1974) 23:1609–1614 disclose a method for destroying endogenous vitamin $B_{12}$ binders and release of bound vitamin $B_{12}$ by heating at alkaline pH in the presence of a reducing agent.

SUMMARY OF THE INVENTION

Methods are provided for pretreating a serum sample to free vitamin $B_{12}$ from endogenous serum binding proteins for subsequent determination of the serum vitamin $B_{12}$ concentration, by incubating the sample with peroxy acid followed by reducing residual peroxy acid with a reductant. The sample may then be used in an assay for the determination of vitamin $B_{12}$.

DESCRIPTION OF THE SPECIFIC EMBODIMENTS

In accordance with the subject invention, methods are provided for making vitamin $B_{12}$ available from endogenous serum binding proteins for subsequent determination of the serum vitamin $B_{12}$ concentration.

In carrying out the subject invention, the vitamin $B_{12}$ is made available by pretreating the serum sample with a peroxy acid such as peroxymonosulfate or peroxytrifluoroacetic acid (including salts, particularly alkali metal salts). Potassium peroxymonosulfate is available from E. I. duPont de Nemours & Company under the trademark OXONE[200]. Peroxytrifluoroacetic acid can be prepared from a mixture of hydrogen peroxide and trifluoroacetic acid. Following treatment of the sample, any unreduced peroxy acid may then be destroyed using a reducing agent which will not interfere with subsequent assay procedures. Reagents for the assay system can be added directly to the pretreated sample.

The sample may be any serum sample. Hemolysis of the sample or lipemia does not affect either the pretreatment or the subsequent assay for vitamin B12.

For use in the pretreatment protocol, the peroxy acid is diluted in a non-interfering buffer such as phosphate buffer, pH 7.0 or citrate buffer, pH 8. The final concentration of peroxy acid in the sample is generally greater than about 10 mM, conveniently between about 25 mM and 100 mM, the concentration of the solution added to the incubation mixture generally being at least 20 mM, preferably 50-100 mM. The sample is incubated with the peroxy acid generally at room temperature for at least 5 minutes, preferably at least 10 minutes although incubation times of 60 minutes or greater do not adversely affect the results.

If the sample will be used in an assay system which uses a specific binding protein to detect vitamin $B_{12}$ present in the sample, it is desirable to reduce any remaining unreduced peroxy acid prior to the addition of specific binding protein. If the assay system uses for example monoclonal anti-$B_{12}$ antibody the reducing agent can be a non-sulfite reducing agent such as methionine, sodium phosphite, sodium arsenite, dithiothreitol, threitol, or $\beta$-mercaptoethanol. If the assay system employed uses a vitamin $B_{12}$ binding protein such as intrinsic factor, the reducing agent can be a sulfite-based reductant such as sodium sulfite, sodium metabisulfite or sodium hydrosulfite or a non-sulfite reducing agent, such as those described above. Binding of vitamin $B_{12}$ is not impaired in the presence of the reducing agent.

Reducing agent is prepared in an appropriate non-interfering buffer such as phosphate buffer, pH 7.0, containing conventional additives to stabilize the reducing agent. The reducing agent may be added to the oxidized sample at room temperature, the final concentration of reducing agent in the sample generally being greater than 5 mM, preferably greater than 10 mM.

The time of incubation of the oxidized sample with the reducing agent is not critical. If the sample is to be used immediately in a vitamin $B_{12}$ assay, any labeled vitamin $B_{12}$ or the binding protein could be combined with the reducing agent for competitive or sequential protocols, respectively.

The pretreatment protocol may be used with a variety of radioassay or non-isotopic methods for the measurement of vitamin $B_{12}$ in serum. These methods include assay protocols which use a binding protein specific for vitamin $B_{12}$, such as monoclonal antibodies or intrinsic factor, either in solution or bound to a solid support. The pretreatment protocol is preferentially combined with a solid phase assay protocol where a binding protein specific for vitamin $B_{12}$ is bound to a solid support. The solid support can be agarose beads such as cyanogen bromide-activated SEPHAROSE, or acrylamide gels such as AFFIGEL. The solid support may be conjugated to the specific binding protein by any conventional means. For a general review of coupling procedures see, for example, Axen et al., Nature (1967) 214:1302-1304. This pretreatment can also be coupled to homogeneous vitamin $B_{12}$ assays based on the complementation of β-galactosidase fragments, in which vitamin $B_{12}$ is conjugated to one of the fragments (enzyme donor) and in which complementation is blocked by B12-enzyme donor conjugate binding to intrinsic factor.

In carrying out the assay using the pretreated sample and solid phase binding protein, any complexes formed between sample vitamin $B_{12}$ and binding protein can be detected by means of a label attached to vitamin B12. Tracer solution can be added to the sample either concomitantly with or subsequent to addition of the reducing agent to the sample. The tracer molecule can be covalently labeled in a number of ways. The label can be an enzyme, for example, alkaline phosphatase, β-D-galactosidase or fragments thereof, glucose-6-phosphate dehydrogenase, glucose oxidase, horseradish peroxidase, urease: a radionuclide, such as $^{57}Co$: a chemiluminescent or fluorescent compound, such as fluorescein isocyanate: or any other label which provides a detectable signal.

The sample containing the labeled vitamin $B_{12}$ is then contacted with the solid phase binding protein. If the intrinsic factor is bound to for example SEPHAROSE, the Sepharose may be in the form of a slurry, preferably a 50% slurry in, for example, 100 mM phosphate buffer, pH 7.5, containing protein such as BSA Bovine Serum Albumin or gelatin. The sample-slurry is then incubated, generally at room temperature for a sufficient time to form B12-intrinsic factor complexes. When the solid support is SEPHAROSE, the incubation mix is preferably rocked during the incubation time to prevent settling of the SEPHAROSE beads. Time of incubation is generally a minimum of 60 minutes at room temperature, although incubation times up to 16 hrs. do not adversely affect the results.

Following incubation, bound and unbound sample can be separated by centrifuging, washing, etc., depending upon the nature of the solid support. The supernatant containin unbound labeled vitamin $B_{12}$ is decanted. Either the solid support containing B12-binding protein complexes or the supernatant may be analyzed to determine the amount of label present. The method of detection will depend on the type of label used as well as the sensitivity required. If the label is a radionuclide, either the solid support or the supernatant may be counted to determine the amount of radioactivity present. When the label is an enzyme, the disappearance of substrate or appearance of reaction product may be measured spectrophotometrically following substrate addition. If the enzyme is, for example, urease, an indicator dye such as cresol red may be used to monitor the change in pH in the sample following addition of enzyme substrate.

Controls may be employed to quantitate the concentration of vitamin $B_{12}$ in a sample. Usually, at least one background solution containing no vitamin $B_{12}$ and at least one serum reference solution containing a known amount of vitamin $B_{12}$ are treated identically to the sample containing an unknown concentration of vitamin $B_{12}$. The amount of label detectable in the background solution is subtracted from the amount of label detectable in the reference solution and the unknown sample. The adjusted values for the reference solution and the unknown sample are then related to determine the amount of vitamin $B_{12}$ present in the sample.

For convenience, the reagents are frequently provided in kits comprising in separate containers the peroxy acid or salt and a reducing agent for use as a pretreatment for serum samples to be used in a vitamin $B_{12}$ assay, and as a vitamin $B_{12}$ assay kit where the peroxy acid or salt and reducing agent are present in conjunction with any one of a labeled vitamin $B_{12}$ solution, binding protein or reference samples comprising a known amount of vitamin $B_{12}$, together with any additional reagents necessary for the performance of the assay. Conveniently, the reagents may be provided in lyophilized form.

The following examples are offered by way of illustration and not by way of limitation.

EXPERIMENTAL

Unless otherwise indicated, in all of the Examples, the approximate concentration in the serum samples for $^{57}Co$-vitamin $B_{12}$ was 0.22 ng/ml (range 0.15 to 0.25 ng/ml), and the approximate concentration for endogenous vitamin $B_{12}$ (i.e., unlabeled) was 0.45 ng/ml.

EXAMPLE 1

Release of $^{57}Co$-$B_{12}$ from Serum by Buffered Peroxymonosulfate

One hundred microliters of peroxymonosulfate in water, 200 mM sodium or potassium phosphate, pH 7.0 or 200 mM sodium citrate (Na Cit.), pH 8.0 was added to 100 μl of serum containing $^{57}Co$-$B_{12}$. The mixture was incubated for 15 min at room temperature in the dark. Two hundred microliters of 100 mM sodium sulfite in 500 mM sodium or potassium phosphate pH 7.0 was then added to reduce any unreduced peroxymonosulfate. The incubation was carried out for 30 min at room temperature in the dark. Five hundred, microliters of human serum albumin-coated charcoal (HSA-Charcoal were added and the mixture incubated for 15 min at room temperature. The mixture was then centrifuged, decanted and the pellet drained. The amount of $^{57}Co$-$B_{12}$ in the pellet was then determined. Peroxymonosulfate is capable of releasing $^{57}Co$-$B_{12}$ and charcoal can precipitate between 75-80% of the released $B_{12}$ with buffered reagent and between 88-92% with unbuffered reagent. These results are shown in Table 1. Unbuffered peroxymonosulfate causes the serum to precipitate and the higher release/precipitation in the unbuffered reagent may be a function of serum protein precipitation and trapping of label.

TABLE 1

Release of Vitamin $B_{12}$ from Serum by Peroxymonosulfate and Separation by HSA-charcoal

| mM Peroxymonosulfate In Pretreatment | % $B_{12}$ Released and Precipitated Peroxymonosulfate in | | |
|---|---|---|---|
| | Water | 200 mM $PO_4$ | 200 mM Na Cit. |
| 0.0 | 13.5 | 10.5 | 8.0 |
| 6.3 | 30.0 | 20.0 | 18.0 |
| 8.0 | 35.0 | 24.0 | 22.5 |
| 10.0 | 48.0 | 29.0 | 27.0 |
| 30.0 | 74.0 | 66.0 | 70.0 |
| 40.0 | 84.0 | 78.0 | 78.0 |
| 50.0 | 92.0 | 82.0 | 80.0 |

EXAMPLE 2

Time Course of $B_{12}$ Release from Serum with Peroxymonosulfate

One hundred microliters of serum containing $^{57}Co$-$B_{12}$ were incubated with 100 ul of 100 mM peroxymonosulfate in water, 200 mM phosphate, pH 7.0, or 200 mM sodium citrate, pH 8.0, for variable time periods at room temperature. Two hundred microliters of 100 mM sodium sulfite in 500 mM sodium or potassium phosphate, pH 7.0, was then added and the mixture incubated for 30 min at room temperature in the dark. Five hundred microliters of HSA-coated charcoal was then added and the mixture incubated for 15 min at room temperature. The sample was then centrifuged, decanted, drained and $^{57}Co$-$B_{12}$ counted. Maximum release/recovery of $^{57}Co$-$B_{12}$ was achieved by 10 min at room temperature. This level was maintained to at least 50 min. These results are shown in Table 2.

TABLE 2

Time Course for Release of Vitamin $B_{12}$ from Serum by Peroxymonosulfate (50 mM)

| Time (Mins) | % $B_{12}$ Released and Precipitated 100 mM Peroxymonosulfate in | | |
|---|---|---|---|
|  | Water | 200 mM $PO_4$ | 200 mM Na Cit. |
| 0.0 | 31.0 | 14.0 | 14.0 |
| 1.3 | 67.5 | 54.0 | 59.0 |
| 5.0 | 73.0 | 67.5 | 73.0 |
| 6.5 | 72.0 | 71.0 | 75.0 |
| 10.0 | 80.0 | 75.0 | 81.0 |
| 16.5 | 85.5 | 76.0 | 79.0 |
| 24.5 | 94.0 | 77.0 | 81.0 |
| 31.0 | 92.0 | 78.5 | 82.5 |
| 52.0 | 93.5 | 85.5 | 79.0 |

Example 3

Comparison of Reducing Agents and the Subsequent Binding of $B_{12}$ by anti-$B_{12}$ Antibody Two hundred microliters of water containing $^{57}Co$-$B_{12}$ were incubated for 15 min at room temperature with 200 μl of a reducing agent. Two concentrations of reducing agent were used, 25 mM and 5 mM. Five hundred microliters of human serum albumin coated charcoal or an anti-$B_{12}$ monoclonal antibody with a secondary antibody precipitating reagent (polyethylene glycol, PEG) were added and the mixture incubated for 15 min at room temperature. Samples were then centrifuged, decanted, drained and counted. As shown in Table 3, neither sulfite nor non-sulfite reducing agents had a significant effect on the charcoal binding of $^{57}Co$-$B_{12}$. Sulfite-based reductants (sodium sulfite, sodium metabisulfite and sodium hydrosulfite) significantly reduced the binding of $B_{12}$ by antibody.

TABLE 3

Comparison of Several Reducing Agents: Effect on Separation Technique

| Reducing Agent | Concentration (mM) | % $B_{12}$ Released and Precipitated | |
|---|---|---|---|
|  |  | HSA-Charcoal | McAb/PEG |
| Methionine | 25 | 98.5 | 83.5 |
|  | 5 | 99.8 | 79.4 |
| Na Sulfite | 25 | 99.9 | 41.8 |
|  | 5 | 96.6 | 55.7 |
| Na Metabisulfite | 25 | 95.7 | 29.8 |
|  | 5 | 96.3 | 55.2 |
| Na Phosphite | 25 | 97.3 | 75.6 |
|  | 5 | 97.7 | 80.4 |
| Na Arsenite | 25 | 97.6 | 80.1 |
|  | 5 | 100.0 | 79.0 |
| Na Hydrosulfite | 25 | 98.0 | 29.3 |
|  | 5 | 97.6 | 56.4 |
| Dithiothreitol | 25 | 98.7 | 82.8 |
|  | 5 | 99.1 | 82.7 |
| β-Mercaptoethanol | 25 | 97.3 | 73.9 |
|  | 5 | 93.3 | 80.4 |
| None | — | 97.9 | 78.2 |

Example 4

Titration of Peroxymonosulfate and Dithiothreitol Concentrations

One hundred microliters of water and 100 μl of peroxymonosulfate in 200 mM phosphate, pH 7.0, were incubated for 15 min at room temperature. Two hundred microliters of dithiothreitol (DTT), 0–200 mM in 100 mM phosphate buffer, 0.01% BSA, pH 7.5, were added and incubated for 10 min at room temperature. Fifty microliters of $^{57}Co$—$B_{12}$ and 8 μl of a 50% slurry of intrinsic factor-Sepharose SEPHAROSE conjugate in 100 mM phosphate buffer, 0.01% BSA pH 7.5, were added and incubated for 60 min at room temperature with rocking. Solutions were then centrifuged, and 300 μl of the supernatant counted. Peroxymonosulfate to dithiothreitol ratios of 1/1 to 1/4 for peroxymonosulfate concentrations of 50 mM or less allow acceptable binding of $B_{12}$ to intrinsic factor-Sepharose. However, if the peroxymonosulfate is not effectively reduced by dithiothreitol, the fraction of released and precipitated $B_{12}$ decreases, indicating the inability of the intrinsic factor-SEPHAROSE to bind the released tracer. These results are shown in Table 4.

TABLE 4

| Fraction of $^{57}Co$—$B_{12}$ Released and Precipitated | | | | | | |
|---|---|---|---|---|---|---|
| Pretreated Sample Peroxymonosulfate Concentration (mM) | [DTT] Concentration (mM) with Pretreated Sample | | | | | |
|  | 0.0 | 6.25 | 12.5 | 25.0 | 50.0 | 100.0 |
| 0.0 | 0.69 | 0.78 | 0.70 | 0.80 | 0.81 | 0.79 |
| 12.5 | — | — | 0.76 | 0.80 | 0.81 | — |
| 25.0 | — | — | 0.69 | 0.77 | 0.76 | — |
| 50.0 | — | — | 0.36 | 0.73 | 0.77 | — |
| 100.0 | — | — | 0.00 | 0.07 | 0.09 | — |

EXAMPLE 5

Effect of Peroxymonosulfate and Dithiothreitol on Vitamin $B_{12}$ Release and Subsequent Binding to Intrinsic Factor-SEPHAROSE One hundred microliters of sample (water, human serum or a synthetic matrix) with added unlabeled vitamin $B_{12}$ of varying concentrations were incubated with 100 μl of 200 mM sodium or potassium phosphate pH 7.0, with or without 50 mM peroxymonosulfate for 15 min at room temperature. Two hundred microliters of 100 mM sodium or potassium phosphate containing 0.01% BSA, pH 7.5, with or without 50 mM dithiothreitol were added and the mixture incubated for 5 min at room temperature. Fifty microliters of $^{57}Co$-$B_{12}$ and 8 μl of 50% slurry of intrinsic factor-SEPHAROSE (IF-SEPHAROSE were added and the mixture incubated for 30 min at room temperature. The samples were then centrifuged and 300 μl of supernatant counted. The results are shown in Table 5.

TABLE 5

The Effect of Peroxymonosulfate and Dithiothreitol on the Release of $B_{12}$ from Matrix Binders and Rebinding by Intrinsic Factor-SEPHAROSE Fraction of $^{57}Co—B_{12}$ Released and Precipitated

| Sample | Peroxymonosulfate | | Dithiothreitol |
|---|---|---|---|
| | 0 μmoles | 5 μmoles | μmoles |
| H₂O | 0.797 | 0.113 | 0 |
| | 0.822 | 0.849 | 10 |
| Serum | 0.047 | 0.237 | 0 |
| | 0.183 | 0.691 | 10 |
| Serum + | 0.303 | 0.198 | 0 |
| 1 ng/ml $B_{12}$ | 0.603 | 0.487 | 10 |
| Synthetic Matrix | 0.572 | 0.107 | 0 |
| | 0.610 | 0.812 | 10 |
| Synthetic Matrix + | 0.330 | 0.121 | 0 |
| 1 ng/ml $B_{12}$ | 0.357 | 0.340 | 10 |

The differences between the untreated samples and those containing both peroxymonosulfate and dithiothreitol indicate the ability of peroxymonosulfate to release vitamin $B_{12}$ from endogenous binders and of intrinsic factor-SEPHAROSE to bind free $B_{12}$ in the reduced system. Samples containing peroxymonosulfate and no dithiothreitol demonstrate that peroxymonosulfate interferes with the binding of $B_{12}$ to intrinsic factor-SEPHAROSE. The similarity between those peroxymonosulfate samples with or without dithiothreitol indicates that the reducing agent does not interfere with $B_{12}$ binding to intrinsic factor-SEPHAROSE under these conditions.

Example 6

Dose Response Curve Generated After Pretreatment With Peroxymonosulfate and Dithiothreitol One hundred microliters of sample (human serum containing unlabeled $B_{12}$, a synthetic matrix containing unlabeled $B_{12}$ or a reference solution containing unlabeled B12) were incubated with 100 μl 50mM peroxymonosulfate in 200 mM phosphate buffer, pH. 7.0, for 15 min at room temperature. Two hundred microliters of 50 mM dithiothreitol in 100 mM phosphate containing 0.01% BSA, pH 7.5, were added and the mixture incubated for 10 min at room temperature. Fifty microliters $^{57}Co$-$B_{12}$ and 8 μl 50% slurry of intrinsic factor-SEPHAROSE were then added and the mixture incubated for 60 min at room temperature with rocking. Samples were centrifuged and 300 μl of supernatant counted. As shown in Table 6, the pretreatment protocol releases serum-bound $B_{12}$ and destroys serum binding protein but does not impair the binding of $B_{12}$ by intrinsic factor-SEPHAROSE. The synthetic matrix and reference solutions do not contain significant quantities of binding proteins and little difference is seen between pretreated and non-pretreated samples.

TABLE 6

Binding of $B_{12}$ to IF-SEPHAROSE Following Pretreatment of Sample with Peroxymonosulfate and Dithiothreitol: Fraction of $B_{12}$ Released and Precipitated

| Concentration of Added Unlabeled $B_{12}$ (pg/ml) | with (+) and without (−) Peroxymonosulfate | | | | | |
|---|---|---|---|---|---|---|
| | Serum | | Matrix | | Reference Samples | |
| | + | − | + | − | + | − |
| 0 | 0.72 | 0.06 | 0.82 | — | 0.81 | 0.78 |
| 150 | 0.75 | — | 0.83 | — | 0.84 | — |
| 250 | 0.73 | 0.09 | 0.80 | 0.80 | 0.83 | 0.75 |
| 500 | 0.73 | — | 0.70 | — | 0.73 | — |

EXAMPLE 7

Timecourse for Reduction of Peroxymonosulfate by Dithiothreitol and Subsequent Binding of $B_{12}$ by Intrinsic Factor-SEPHAROSE One hundred microliters of sample (water, synthetic matrix or human serum) were incubated with 100 μl 50 mM peroxymonosulfate in 200 mM phosphate buffer, pH 7.0, for 15 min at room temperature. Two hundred microliters of 50 mM dithiothreitol in 100 mM phosphate buffer containing 0.01% BSA, pH 7.5, were added and the samples incubated at room temperature for variable time periods. Fifty microliters $^{57}Co$–$B_{12}$ and 8 μl 50% slurry of intrinsic factor-SEPHAROSE were added for variable times and the mixture incubated at room temperature with rocking. Samples were then centrifuged and 300 μl of supernatant was counted. As shown in Table 7, reduction of peroxymonosulfate is apparently instantaneous indicating that $^{57}Co$-$B_{12}$ tracer or the intrintaneous factor-SEPHAROSE could be combined with the dithiothreitol for competitive or sequential protocols, respectively.

TABLE 7

Effect of Time of Incubation with Dithiothreitol on Binding to IF-SEPHAROSE*: Fraction of $B_{12}$ Released and Precipitated

| Time for DTT Incubation (min) | Sample | | | |
|---|---|---|---|---|
| | Water | Matrix | Matrix + 1000 pg/ml $B_{12}$ | Serum |
| 0 | 0.87 | 0.81 | 0.54 | 0.75 |
| 2 | 0.86 | 0.81 | 0.46 | 0.72 |
| 5 | 0.87 | 0.81 | 0.49 | 0.74 |
| 10 | 0.86 | 0.81 | 0.49 | 0.75 |
| 15 | 0.85 | 0.82 | 0.49 | 0.73 |

*All samples were incubated with IF-SEPHAROSE for 60 minutes.

As shown in Table 8, the binding reaction of $B_{12}$ with intrinsic factor-SEPHAROSE approaches completion by 1 hr under the conditions used.

TABLE 8

Effect of Time of Incubation with IF-SEPHAROSE on $B_{12}$ Binding to IF-SEPHAROSE*: Fraction of $B_{12}$ Released and Precipitated

| Time of Incubation With IF-SEPHAROSE (min) | Sample | | | |
|---|---|---|---|---|
| | Water | Matrix | Matrix + 1000 pg/ml $B_{12}$ | Serum |
| 15 | 0.63 | 0.63 | 0.34 | 0.50 |
| 30 | 0.79 | 0.74 | 0.37 | 0.63 |
| 45 | 0.81 | 0.79 | 0.40 | 0.67 |
| 60 | 0.86 | 0.82 | 0.40 | 0.66 |

*All samples were incubated with dithiothreitol for 15 minutes

The subject methods provide a rapid and simple means for pretreating a serum sample for subsequent determination of vitamin $B_{12}$ concentration. The pretreatment may be used prior to a variety of radioassay or non-isotopic methods for the measurement of vitamin $B_{12}$ in serum.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. In a method for determining the vitamin $B_{12}$ concentration in a serum sample, wherein said method comprises incubating said sample with labeled vitamin $B_{12}$ and a vitamin $B_{12}$-specific binding protein to form labeled vitamin $B_{12}$- specific binding protein complexes; separating any unbound labeled vitamin $B_{12}$ from said labeled vitamin $B_{12}$-specific binding complexes; and detecting any labeled vitamin $B_{12}$-specific binding protein complexes or unbound labeled vitamin $B_{12}$, the improvement which comprises:

pretreating the serum sample by contacting said sample with an oxidizing agent consisting essentially of a peroxy acid or salt thereof to release vitamin $B_{12}$ from substantially all endogenous binding proteins present in said sample to make vitamin $B_{12}$ available for detection by binding to said vitamin-$B_{12}$ specific binding protein in said method.

2. A method according to claim 1, said improvement further comprising:

subsequent to said contacting, adding a sufficient amount of a reducing agent to said oxidized sample to substantially reduce any unreduced peroxy acid or salt thereof prior to use of said oxidized sample in said method.

3. A method according to claim 2, wherein said reducing agent is dithiothreitol.

4. A method according to claim 1, wherein said peroxy acid or salt thereof is peroxymonosulfuric acid or peroxytrifluoroacetic acid or their salts.

5. In a method for determining the vitamin $B_{12}$ concentration in a serum sample, wherein said method comprises incubating said sample with labeled vitamin $B_{12}$ and a vitamin $B_{12}$ specific binding protein to form labeled vitamin $B_{12}$-specific binding protein complexes; separating any unbound labeled vitamin $B_{12}$ from said labeled vitamin $B_{12}$-specific binding protein complexes; and detecting any labeled vitamin $B_{12}$-specific binding protein complexes or unbound labeled vitamin $B_{12}$, the improvement which comprises:

prior to said incubating, contacting said sample with an oxidizing agent consisting essentially of peroxymonosulfuric acid or its salt to release vitamin $B_{12}$ from substantially all endogenous binding proteins present in said sample to make vitamin $B_{12}$ available for detection by binding to said vitamin $B_{-12}$ specific binding protein; and subsequent to said contacting, adding a sufficient amount of a reducing agent to said oxidized sample to reduce any unreduced peroxymonosulfuric acid or its salts.

6. A method according to claim 5, wherein said vitamin $B_{12}$ specific binding protein is intrinsic factor.

7. A method according to claim 6, wherein said intrinsic factor is bound to a solid support.

8. A vitamin $B_{12}$ assay kit comprising as components for said assay;

(a) an oxidizing agent consisting essentially of peroxymonosulfate;

(b) dithiothreitol; and (c) at least one of a vitamin $B_{12}$ specific binding protein, a labeled vitamin $B_{12}$ tracer, or at least one reference sample comprising a known concentration of vitamin $B_{12}$, wherein (a) and (b) are in separate containers.

9. A vitamin $B_{12}$ assay kit according to claim 8, wherein said specific binding protein is intrinsic factor.

10. A vitamin $B_{12}$ assay kit according to claim 9, wherein said intrinsic factor is bound to a solid support.

11. A vitamin $B_{12}$ assay kit according to claim 8, wherein said components are lyophilized.

* * * * *